(12) United States Patent
Retsina et al.

(10) Patent No.: US 8,785,155 B2
(45) Date of Patent: *Jul. 22, 2014

(54) PROCESS FOR OBTAINING BIOCHEMICALS IN A ZERO-LIQUID DISCHARGE PLANT

(75) Inventors: Theodora Retsina, Atlanta, GA (US); Vesa Pylkkanen, Atlanta, GA (US); Kimberly Nelson, Atlanta, GA (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 277 days.

This patent is subject to a terminal disclaimer.

(21) Appl. No.: 13/471,662

(22) Filed: May 15, 2012

(65) Prior Publication Data

US 2013/0130318 A1    May 23, 2013

Related U.S. Application Data

(63) Continuation of application No. 12/474,267, filed on May 28, 2009, now Pat. No. 8,211,680.

(51) Int. Cl.
| | | |
|---|---|---|
| *C12P 19/00* | (2006.01) | |
| *C12P 7/16* | (2006.01) | |
| *C12P 7/06* | (2006.01) | |
| *C12P 7/14* | (2006.01) | |
| *C12P 7/08* | (2006.01) | |
| *C12P 7/10* | (2006.01) | |
| *C12P 7/54* | (2006.01) | |
| *C07C 53/00* | (2006.01) | |
| *C13K 1/02* | (2006.01) | |
| *C07C 51/47* | (2006.01) | |
| *C12P 19/02* | (2006.01) | |

(52) U.S. Cl.
CPC . *C07C 51/47* (2013.01); *C12P 7/10* (2013.01); *Y02E 50/10* (2013.01); *C12P 7/16* (2013.01); *Y02E 50/17* (2013.01); *Y02E 50/16* (2013.01); *C12P 19/02* (2013.01)
USPC ............. 435/72; 435/160; 435/161; 435/162; 435/163; 435/165; 435/140; 562/512; 127/37

(58) Field of Classification Search
USPC ........... 435/72, 160, 161, 162, 163, 165, 140; 562/512; 127/37
See application file for complete search history.

(56) References Cited

U.S. PATENT DOCUMENTS

| | | |
|---|---|---|
| 7,074,603 B2 | 7/2006 | Verser et al. |
| 8,211,680 B2 * | 7/2012 | Retsina et al. ................ 435/165 |
| 2008/0102502 A1 | 5/2008 | Foody et al. |
| 2008/0248540 A1 | 10/2008 | Yang |

FOREIGN PATENT DOCUMENTS

WO    2007048879 A1    5/2007

* cited by examiner

*Primary Examiner* — Ganapathirama Raghu
(74) *Attorney, Agent, or Firm* — Ryan P. O'Connor

(57) ABSTRACT

A method is presented for the production of cellulosic ethanol, acetic acid and derivatives from the extract containing fibers and hemicelluloses after steam cooking of biomass in a host plant. The process is integrated with the host plant process to minimize the effect of loss of heat value from the extracted hemicelluloses and eliminate the need for the waste water treatment plant.

20 Claims, 2 Drawing Sheets

| Concentration, mg/mL | | | |
|---|---|---|---|
| | As Received | After Hydrolysis | After Fermentation |
| Acetic Acid | 0.588 | 0.667 | 1.182 |
| 5-HMF | 0.022 | 0.019 | 0.039 |
| Furfural | 0 | 0 | 0 |
| Cellubiose | 0.1 | 0.42 | 1.8 |
| Glucose | 0.61 | 1.664 | 0 |
| Mannose | ND | 0.449 | 0 |
| Galactose | 0.06 | 2.231 | 0.75 |
| Xylose | 0.08 | 5.406 | 3.967 |
| Arabinose | 0.25 | 0.947 | 1.146 |
| Total Sugars | 1 | 10.697 | 5.863 |
| Ethanol | N/A | N/A | 1.352 |

Figure 2

PROCESS FOR OBTAINING BIOCHEMICALS IN A ZERO-LIQUID DISCHARGE PLANT

PRIORITY DATA

This patent application is a continuation application of U.S. Pat. No. 8,211,680, issued Jul. 3, 2012, which is hereby incorporated by reference herein.

FIELD OF THE INVENTION

This invention relates, in general, to the post treatment of effluent from forest product or food or beverage plant. The treatment specifically converts the soluble fraction of extracted lignocellulosic material to byproduct ethanol, acetic acid and other chemicals.

BRIEF DESCRIPTION OF THE DRAWINGS

A more complete understanding of the present invention may be obtained by reference to the following detailed description when read in conjunction with the accompanying drawings wherein:

FIG. 2 shows concentrations of acetic acid and other wood derived components after hydrolysis and fermentation of treatment of effluent from steam cooking of mixed hardwood chips.

BACKGROUND OF THE INVENTION

Figure 1:
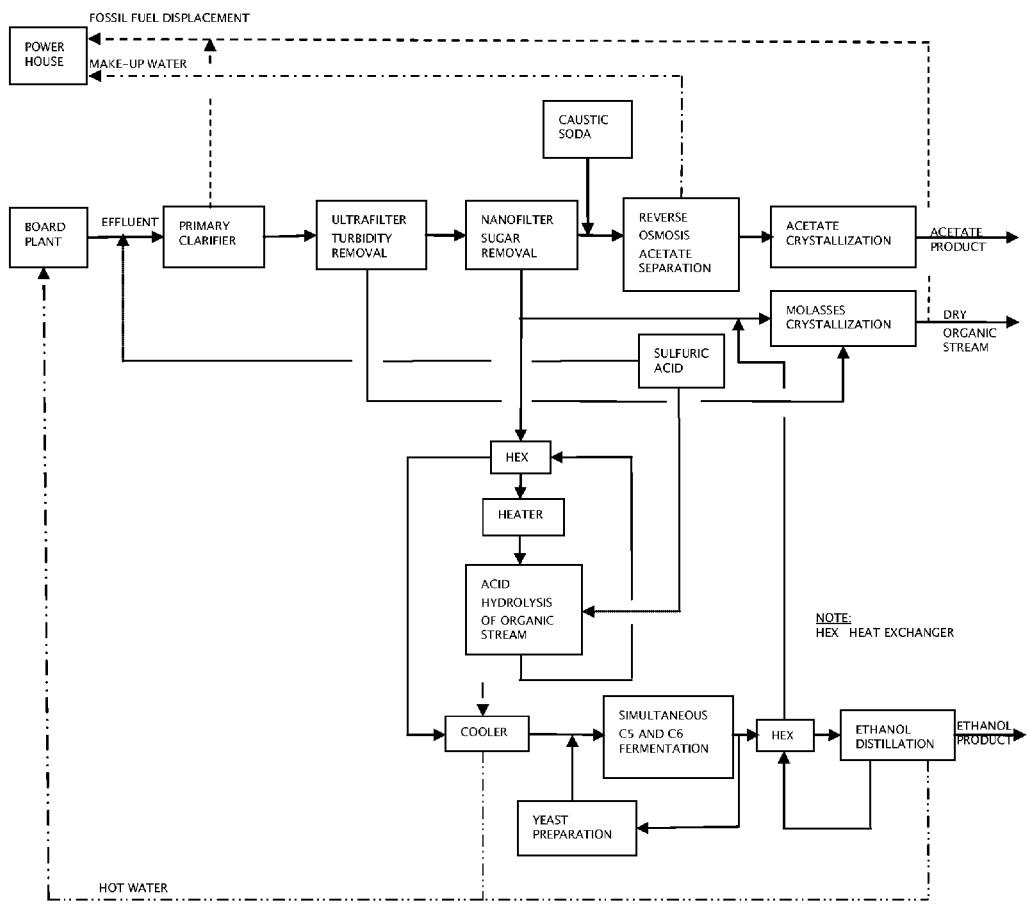
FIG. 1 illustrates a typical general arrangement of the unit operations for mixed hardwood derived extract from steam cooking water effluent. Other effluent liquors are possible. Process steps may be in other sequences.

Forest products industry effluents contain dissolved or mechanically separated wood components. The major wood components are lignin, hemicelluloses and cellulose. The pulping processes preferably separate lignin and hemicelluloses. The dissolved lignin and hemicelluloses are burned for process energy and chemical recovery in the most pulping processes. Some of the fibers and dissolved wood components escape the process to the effluent treatment plant. The recovery, separation, and upgrade of the degraded hemicelluloses into chemicals and derivatives are currently not practiced. These hemicelluloses are most commonly consumed during activated sludge wastewater treatment. The activated sludge is then land filled or burned.

Specifically, the steam cooking process dissolves predominantly hemicelluloses in temperatures above 160 degrees C. The solution containing hemicelluloses removed from this process is termed extract. The extraction of hemicelluloses using steam cooking and blowing through pressure reducing valve, commonly termed "blow valve", is used in the production of medium and hard density board. Because of the low concentration of hemicelluloses in the extract, when the hemicelluloses are hydrolyzed to sugars, the subsequent concentration of sugars through evaporation before fermentation to produce ethanol is energy intensive.

Research indicates that ethanol, acetic acid and their byproducts can be derived from the extract. Especially, predominantly hardwood, containing bark, produces extract rich in acetic acid and sugars as taught by Amidon et al. in (U.S. Patent Application No. 2007/0079944 A1, Apr. 12, 2007).

The present inventors have now developed a process wherein the hemicelluloses in the extract can be converted to chemical products in an energy efficient process.

SUMMARY OF THE INVENTION

The present invention describes a process for the production of ethanol, acetic acid and derivatives from hemicelluloses extracted from steam exploded biomass. Treating the hemicelluloses extracted through a series of membranes, hydrolysis, fermentation and distillation recovers saleable products. The process is integrated with the host plant to reuse water and minimize process energy consumption and eliminate the need for the waste water treatment plant.

DETAILED DESCRIPTION OF THE INVENTION

Biomass is heated in a batch or continuous digesting vessel with steam and blown through a valve commonly termed "blow valve". The blown chips are washed with water to recover the dissolved lignocellulosic components, termed "extract", into the wash filtrate. For wood chips biomass, the wash filtrate contains fibers, some dissolved lignins and hemicelluloses derivatives, i.e., xylan, glucan, mannan, arbinan, galactan, and acetic acid. The wash filtrate is at approximately 2% solids concentration at 50 degrees C. temperature is clarified and diverted to the membranes. The remaining biomass is sent to a board or pulping process digester where it is converted to final product.

The first step of the process is sedimentation. The wash filtrate is clarified from suspended material, such as fiber and sand by clarification or centrifugation. From the sedimentation, the clarified filtrate is then sent to the ultrafiltration step. The suspended solids are further concentrated in a filter press to form combustible product. At this point the clarified filtrate may be acidified to increase acetic acid yield and reduce microbial fouling of the membranes.

The second step of the process is ultrafiltration of the large molecules for lignin removal. The clarified filtrate leaving the sedimentation is sent to a bank of ultrafiltration membrane elements. The ultrafiltration membrane reject large dissolved molecules, such as lignin at molecular weight cutoff between MW=3,000 and MW=10,000. The concentrate from the ultrafiltration membrane is combined with the suspended solids and combusted.

The third step of the process is nanofiltration for sugar molecule removal. The permeate from ultrafiltration is sent to a nanofiltration membrane skid, where the molecules over MW=100 are concentrated. These molecules are predominantly wood hemicelluloses and sugars. The sugars are sent to hydrolysis, while the membrane permeate is sent to acetic acid separation.

The fourth step is reverse osmosis filtration. To recover the acetic acid from the nanofiltration permeate, reverse osmosis membranes are used in alkaline environment to convert acetic acid to acetate form. The reverse osmosis membrane permeate is clean water, because of good rejection of other molecules in alkaline conditions as demonstrated by Mukhopadhyay (U.S. Pat. No. 6,537,456, Mar. 25, 2003). In another version of the process acetic acid is separated in an acetic environment. The concentrated acetate can be sold as liquefied de-icing product or be further concentrated by evaporation for sale as an acetate product.

The fifth step of the process is acid hydrolysis. Sulfuric acid or enzymes can be used to hydrolyze the sugar concentrate from the nanofiltration membrane, which is rich in sugars and hemicelluloses, into hydrolyzate containing fermentable sugars. The hydrolysis reactors will be operated to give a continuous flow of hydrolyzate going to the fermentation and separations sections of the plant. The reaction conditions for the acid hydrolysis will be 30 to 120 minutes residence time at a temperature of 80 to 180 degrees C. The pH of the solution during hydrolysis will be 0.1 to 4 pH. This low pH will convert polymer hemicelluloses into monomer sugars. Time, temperature and pH must be optimized to maximize sugar yield without converting monomer sugars further to furfural and 5-hydroxy-2-methylfurfural, which inhibit fermentation. Alternatively, a mixture of cellulase and xylanase enzymes can be used to perform hydrolysis.

The sixth step of the process is fermentation of biomass-derived sugars. Fermentation of the fermentable sugars in the hydrolyzate is performed in a multi-stage semi-continuous process with a micro-organism capable of converting five and six carbon sugars into ethanol and carbon dioxide. Acetic acid product or ammonium hydroxide is used for the pH adjustment and nutrients. Additional nutrients and yeast are added in a recirculation line for the first fermentation stage. Carbon dioxide is removed from the fermenters and scrubbed with liquid for alcohol recovery and odor control. The product, commonly termed "beer", from the fermentation stage is sent to distillation in the ethanol column.

The seventh step of the process is distillation of ethanol. The beer from the fermentation process is sent to a distillation column to separate the ethanol from the residual sugars that were not fermented. Ethanol leaves as the overhead product from the distillation column and is recovered at approximately 50% concentration. The final concentration of the ethanol product is performed in a rectifying column and molecular sieves to obtain over 99% ethanol concentration. Alternatively, membranes are used for final concentration. All ethanol distillation columns are designed for continuous operation. The distillation bottoms are evaporated to achieve a zero liquid discharge plant operation.

Integration of the biorefinery with the existing plant. Process integration of the biorefinery with the existing plant site is very important as it improves both the capital as well as the operating cost of the proposed installation. The water from the reverse osmosis step is used for boiler feedwater makeup or any other fresh water use point. Water reuse also decreases the heating needs of the host plant.

In this process, activated sludge is not burned, causing a decrease in the steam produced in the existing plant biomass boiler. However, this steam loss is mitigated by the reduction in energy required by the waste water plant and the host plant where less water heating is required due to the recycle of hot water from the reverse osmosis step.

EXAMPLE 1

The pH of 125 mL of extract from the steam cooking of hardwood chips was adjusted to 1 by adding 95% sulfuric acid. The extract was then hydrolyzed at 120 degrees C. for 1 hour in an autoclave. The pH of the hydrolyzed liquor was adjusted tp 5.6 using ammonium hydroxide (30% ammonia). The liquor was then combined with 3 g peptone and 1.5 g yeast extract nutrients. 15 g of this solution was combined with 3 g yeast and inoculated at 30 degrees C. for 4 hours. The inoculated solution was recombined with the original and fermented at 35 degrees C. for 4 hours. FIG. 2 shows the concentration of acetic acid, ethanol, and other wood derived components for the extract as received, after hydrolysis, and after fermentation.

The invention claimed is:

1. A process for producing fermentable sugars and acetic acid from a biomass-derived extract, said process comprising:
    (a) providing a liquid extract produced during steam or hot-water cooking of biomass, wherein said liquid extract comprises hemicelluloses, acetic acid, dissolved lignin, and suspended solids;
    (b) clarifying said liquid extract by sedimentation or centrifugation for removing said suspended solids, to produce a clarified extract comprising said hemicelluloses and said acetic acid;
    (c) introducing said clarified extract to an ultrafiltration unit for removing said dissolved lignin with a molecular-weight cutoff range of 3,000 g/mol to 10,000 g/mol, to produce an ultrafiltration concentrate comprising said dissolved lignin and an ultrafiltration permeate comprising said hemicelluloses and said acetic acid;
    (d) introducing said ultrafiltration permeate to a nanofiltration unit for removing said hemicelluloses, to produce a nanofiltration concentrate comprising said hemicelluloses and a nanofiltration permeate comprising said acetic acid;
    (e) introducing said nanofiltration permeate to a reverse-osmosis membrane, to produce a reverse-osmosis permeate comprising water and a reverse-osmosis concentrate comprising said acetic acid; and
    (f) introducing said nanofiltration concentrate to a hydrolysis reactor, to produce a hydrolyzate comprising fermentable sugars.

2. The process of claim 1, wherein said clarified extract is acidified prior to step (c).

3. The process of claim 1, wherein said suspended solids are recovered as a combustion fuel.

4. The process of claim 1, wherein said dissolved lignin is recovered as a combustion fuel.

5. The process of claim 1, wherein said ultrafiltration concentrate is combined with said suspended solids to form a combustion fuel mixture.

6. The process of claim 1, wherein said nanofiltration unit comprises a membrane with a molecular-weight cutoff of 100 g/mol.

7. The process of claim 1, wherein said reverse-osmosis permeate consists essentially of water.

8. The process of claim 1, wherein said reverse-osmosis permeate is used as boiler feedwater.

9. The process of claim 1, wherein said reverse-osmosis permeate is recycled for use in said steam or hot-water cooking of biomass.

10. The process of claim 1, wherein said hydrolysis reactor is operated in the presence of sulfuric acid at a pH selected from 0.1 to 4, a hydrolysis temperature selected from 80° C. to 180° C., and a hydrolysis time selected from 30 minutes to 2 hours.

11. The process of claim 1, wherein said hydrolysis reactor is operated in the presence of a mixture of cellulase and xylanase enzymes.

12. The process of claim 1, said process further comprising fermentation of said fermentable sugars to produce a fermentation product.

13. The process of claim 12, wherein said fermentation product is ethanol.

14. The process of claim 12, wherein said fermentation product is butanol.

15. The process of claim 12, said process further comprising distillation of said fermentation product, wherein distillation bottoms are recycled or evaporated rather than discharged as liquid.

16. The process of claim 15, said process further comprising recycling said reverse-osmosis permeate and recycling cooling water used for cooling said hydrolyzate, to achieve a zero-liquid-discharge process.

17. A process for producing an alcohol and acetic acid from a biomass-derived extract, said process comprising:
   (a) providing a liquid extract produced during steam or hot-water cooking of biomass, wherein said liquid extract comprises hemicelluloses, acetic acid, dissolved lignin, and suspended solids;
   (b) clarifying said liquid extract by sedimentation or centrifugation for removing said suspended solids, to produce a clarified extract comprising said hemicelluloses and said acetic acid;
   (c) introducing said clarified extract to an ultrafiltration unit for removing said dissolved lignin with a molecular-weight cutoff range of 3,000 g/mol to 10,000 g/mol, to produce an ultrafiltration concentrate comprising said dissolved lignin and an ultrafiltration permeate comprising said hemicelluloses and said acetic acid;
   (d) introducing said ultrafiltration permeate to a nanofiltration unit for removing said hemicelluloses, to produce a nanofiltration concentrate comprising said hemicelluloses and a nanofiltration permeate comprising said acetic acid;
   (e) introducing said nanofiltration permeate to a reverse-osmosis membrane, to produce a reverse-osmosis permeate comprising water and a reverse-osmosis concentrate comprising said acetic acid;
   (f) introducing said nanofiltration concentrate to a hydrolysis reactor, to produce a hydrolyzate comprising fermentable sugars; and
   (g) fermenting said fermentable sugars to an alcohol.

18. The process of claim 17, wherein said alcohol is ethanol.

19. The process of claim 17, wherein said alcohol is butanol.

20. A process for producing acetic acid from a biomass-derived extract, said process comprising:
   (a) providing a liquid extract produced during steam or hot-water cooking of biomass, wherein said liquid extract comprises hemicelluloses, acetic acid, dissolved lignin, and suspended solids;
   (b) clarifying said liquid extract by sedimentation or centrifugation for removing said suspended solids, to produce a clarified extract comprising said hemicelluloses and said acetic acid;
   (c) introducing said clarified extract to an ultrafiltration unit for removing said dissolved lignin with a molecular-weight cutoff range of 3,000 g/mol to 10,000 g/mol, to produce an ultrafiltration concentrate comprising said dissolved lignin and an ultrafiltration permeate comprising said hemicelluloses and said acetic acid;
   (d) introducing said ultrafiltration permeate to a nanofiltration unit for removing said hemicelluloses, to produce a nanofiltration concentrate comprising said hemicelluloses and a nanofiltration permeate comprising said acetic acid;
   (e) introducing said nanofiltration permeate to a reverse-osmosis membrane, to produce a reverse-osmosis permeate comprising water and a reverse-osmosis concentrate comprising said acetic acid; and
   (f) recovering said acetic acid.

* * * * *